United States Patent
Hallbäck

(10) Patent No.: US 11,331,445 B2
(45) Date of Patent: May 17, 2022

(54) DETERMINATION OF NEUROMUSCULAR EFFICIENCY DURING MECHANICAL VENTILATION

(71) Applicant: MAQUET CRITICAL CARE AB, Solna (SE)

(72) Inventor: Magnus Hallbäck, Danderyd (SE)

(73) Assignee: MAQUET CRITICAL CARE AB, Solna (SE)

( * ) Notice: Subject to any disclaimer, the term of this patent is extended or adjusted under 35 U.S.C. 154(b) by 390 days.

(21) Appl. No.: 16/479,184

(22) PCT Filed: Feb. 3, 2017

(86) PCT No.: PCT/SE2017/050096
§ 371 (c)(1),
(2) Date: Jul. 18, 2019

(87) PCT Pub. No.: WO2018/143844
PCT Pub. Date: Aug. 9, 2018

(65) Prior Publication Data
US 2019/0351166 A1  Nov. 21, 2019

(51) Int. Cl.
*A61M 16/00* (2006.01)
*A61B 5/087* (2006.01)
(Continued)

(52) U.S. Cl.
CPC .......... *A61M 16/024* (2017.08); *A61B 5/087* (2013.01); *A61B 5/389* (2021.01); *A61B 5/4041* (2013.01);
(Continued)

(58) Field of Classification Search
CPC .............. A61M 16/00; A61M 16/0051; A61M 16/0057; A61M 16/022; A61M 16/024;
(Continued)

(56) References Cited

U.S. PATENT DOCUMENTS

| 5,107,830 A | 4/1992 | Younes |
| 8,720,441 B2 | 5/2014 | Sinderby |

(Continued)

FOREIGN PATENT DOCUMENTS

| CN | 1960671 A | 5/2007 |
| CN | 102202574 A | 9/2011 |

(Continued)

OTHER PUBLICATIONS

Bellani et al., "Estimation of Patient's Inspiratory Effort From the Electrical Activity of the Diaphragm", Society of Critical Care Medicine and Lippincott Williams & Wilkins, vol. 41, No. 6, Jun. 2013, 9 sheets.

(Continued)

*Primary Examiner* — Joseph D. Boecker
(74) *Attorney, Agent, or Firm* — Fay Kaplun & Marcin, LLP

(57) ABSTRACT

A method, a computer program and a breathing apparatus relates to determination of at least one physiological parameter including the neuromechanical efficiency [NME] of a patient being mechanically ventilated by the breathing apparatus. This is achieved by obtaining samples of an airway pressure ($P_{aw}$), a patient flow (Ø), a change in lung volume (V) caused by the patient flow, and an electrical activity of a respiratory muscle of the patient, during ventilation of the patient at a first level of ventilatory assist and a second and different level of ventilatory assist, and determining the at least one physiological parameter, including NME, from the airway pressure samples, the patient flow samples, the samples of the change in lung volume, and the samples of the electrical activity of the respiratory muscle, obtained at the different levels of ventilatory assist.

25 Claims, 2 Drawing Sheets

(51) Int. Cl.
*A61B 5/00* (2006.01)
*A61B 5/389* (2021.01)
*A61B 5/091* (2006.01)
*A61M 16/20* (2006.01)

(52) U.S. Cl.
CPC ....... *A61B 5/4836* (2013.01); *A61M 16/0051* (2013.01); *A61B 5/091* (2013.01); *A61M 16/0057* (2013.01); *A61M 16/20* (2013.01); *A61M 2016/003* (2013.01); *A61M 2016/0027* (2013.01); *A61M 2205/3303* (2013.01); *A61M 2210/1014* (2013.01); *A61M 2230/08* (2013.01)

(58) Field of Classification Search
CPC .... A61M 2016/0027; A61M 2016/003; A61M 2205/3303; A61M 2210/1014; A61M 2230/08; A61B 5/389; A61B 5/4041; A61B 5/4836
See application file for complete search history.

(56) References Cited

U.S. PATENT DOCUMENTS

| | | | | |
|---|---|---|---|---|
| 2003/0188748 | A1* | 10/2003 | Sinderby | A61M 16/026 128/204.21 |
| 2011/0301482 | A1* | 12/2011 | Sinderby | A61B 5/091 600/529 |
| 2012/0103334 | A1* | 5/2012 | Sinderby | A61B 5/08 128/204.18 |
| 2017/0128684 | A1* | 5/2017 | Sinderby | A61M 16/024 |
| 2019/0015615 | A1* | 1/2019 | Sinderby | A61M 16/024 |

FOREIGN PATENT DOCUMENTS

| | | |
|---|---|---|
| CN | 102355857 A | 2/2012 |
| WO | 2007/082384 | 7/2007 |
| WO | 2007/082384 A1 | 7/2007 |

OTHER PUBLICATIONS

Goligher, "Diaphragm Activity and Function During Mechanic Ventilation", Department of Physiology University of Toronto, 2016, 208 sheets.

Vitacca et al., "Assessment of Physiologic Variables and Subjective Comfort Under Different Levels of Pressure Support Ventilation", Chest, Sep. 2004, vol. 126, pp. 851-859.

* cited by examiner

DETERMINATION OF NEUROMUSCULAR EFFICIENCY DURING MECHANICAL VENTILATION

TECHNICAL FIELD

The present invention generally relates to the field of mechanical ventilation. More specifically, the present invention relates to a breathing apparatus, a method and a computer program for determining physiological parameters, including the neuromechanical efficiency (NME), of a mechanically ventilated patient.

BACKGROUND

Mechanical ventilation can be used to provide ventilatory assist to spontaneously breathing patients, for example by means of a mechanical ventilator.

In recent years there has evolved techniques for neurally adjusted ventilation, i.e., techniques in which the ventilation pattern provided to the patient by the ventilator is adapted to the breathing efforts of the patient by controlling the supply of breathing gas by the ventilator based on bioelectrical signals indicating at least the points in time at which there is a desire of the patient to inhale and/or exhale. An example of such a technique is the now clinically well-established technique of neurally adjusted ventilatory assist (NAVA).

The act of taking a breath is controlled by the respiratory centre of the brain, which decides the characteristics of each breath, including timing and size. The respiratory centre sends a signal along the phrenic nerve, excites the diaphragm muscle cells, leading to muscle contraction and descent of the diaphragm dome. As a result, the pressure in the airway drops, causing an inflow of air into the lungs.

With NAVA, the electrical activity of the diaphragm (Eadi) is captured, fed to a NAVA-enabled ventilator and used to assist the patient's breathing in synchrony with and in proportion to the patient's own breathing efforts. As the work of the ventilator and the diaphragm is controlled by the same signal, coupling between the diaphragm and the NAVA-enabled ventilator is synchronized simultaneously.

A challenge with neurally adjusted ventilatory assist is to adequately determine the level of unloading of the patient's respiratory muscles or the patient's contribution to the inspiration when both mechanical ventilatory assist and the patient's own inspiratory muscles contribute to the inspiration. Even though methods for predicting unloading of the patient's respiratory muscles and the resistive and elastic load caused by the patient's respiratory system have been proposed, they still present the drawbacks of failing to show the patient's neural effort and neglecting the effect of the patient's muscle weakness.

This challenge is addressed by Bellani et al. in "Estimation of patient's inspiratory effort from the electrical activity of the diaphragm", Crit Care Med. 2013 June; 41(6):1483-91. doi: 10.1097/CCM.0b013e31827caba0. Bellani et al. suggests an index relating the pressure generated by the respiratory muscles to the electrical activity of the diaphragm (Eadi) to be calculated from Eadi and airway pressure during an expiratory occlusion, in order to estimate the patient's inspiratory effort. This index (referred to as Pmusc/Eadi index in Bellani et al.) is a proportionality coefficient relating the Eadi to the pressure generated by the diaphragm and so constitutes a measure of the neuromechanical efficiency (NME) of the diaphragm. This and other indices relating the electrical activity of a respiratory muscle to the pressure generated by the respiratory muscle will hereinafter be referred to as NME.

A problem associated with the method disclosed in Bellani et al. is that it relies on expiratory occlusion manoeuvres. An occlusion manoeuvre is a rather drastic intervention reducing the efficiency of the ongoing ventilatory treatment and causing discomfort to the ventilated patient. Furthermore, although being a useful approximation, an NME index that is statically determined during an occlusion manoeuvre is not an accurate measure of the neuromechanical efficiency of the respiratory muscle during normal, dynamic conditions.

The above mentioned challenge is also addressed by Sinderby in U.S. Pat. No. 8,720,441, "Determining patient-ventilator breath contribution index in spontaneously breathing mechanically ventilated patients". Sinderby discloses a method for determining a patient-ventilator breath contribution (PVBC) index based on a relation between the patient's efficiency to generate an inspiratory volume without mechanical ventilatory assist and the patient's efficiency to generate an inspiratory volume with mechanical ventilatory assist. More specifically, the PVBC index is determined based on the electrical activity of a patient's respiratory muscle (e.g., the diaphragm) during inspiration and the patient's inspiratory volume, for example the tidal inspiratory volume. The PVBC index is determined by comparing the ratio between the tidal inspiratory volume and the electrical activity of the patient's respiratory muscles during no ventilatory assist with the ratio between the tidal inspiratory volume and the electrical activity of the patient's respiratory muscles during ventilatory assist.

A problem associated with the method disclosed in Sinderby is that it requires the electrical activity of the patient's respiratory muscle during no respiratory assist (zero assist) to be determined. This means that the method requires intermittent periods of no, or nearly no, ventilatory assist. Consequently, the method cannot always be performed while at the same time ensuring adequate ventilatory treatment of the patient.

Thus, there is a need for alternative methods allowing NME to be determined dynamically without occlusion manoeuvres, zero-assist manoeuvres or other aggressive interventions.

SUMMARY

The present invention relates to an apparatus and method for determination of the neuromechanical efficiency (NME) of a spontaneously breathing, mechanically ventilated patient.

In particular, the present invention relates to an apparatus and method for determining NME dynamically, i.e., during non-static conditions, in order to obtain an NME value that more adequately reflects the real neuromechanical efficiency of the respiratory muscles of the patient than a corresponding value obtained during static conditions, such as during an occlusion manoeuvre.

In addition, the present invention relates to an apparatus and method capable of determining NME during ongoing ventilatory treatment of a patient with a minimum of influence on the patient and the ongoing treatment.

Furthermore, the present invention relates to an apparatus and method that are capable of determining the resistive and elastic status of the respiratory system of the patient, with a minimum of influence on the patient and the ongoing treatment.

According to one aspect of the present disclosure, these and other objects are met by a method for determination of at least one physiological parameter, including the NME, of a patient connected to a breathing apparatus providing ventilatory assist to the patient. The method comprises a step of obtaining samples of an airway pressure, a patient flow, a change in lung volume caused by the patient flow and an electrical activity of a respiratory muscle of the patient during ventilation of the patient at a first level of ventilatory assist and at least a second and different level of ventilatory assist. Both the first and the at least second levels of ventilatory assist may be above a zero level of ventilatory assist, and also above any level of ventilatory assist provided by the mere application by the breathing apparatus of a positive end-expiratory pressure (PEEP) to the patient. The method further comprises the step of determining the at least one physiological parameter, including NME, from the airway pressure samples, the patient flow samples, the samples of the change in lung volume and the samples of the electrical activity of the respiratory muscle, obtained at the different levels of ventilatory assist.

The proposed method allows for NME determination during relatively high levels of ventilatory assist, i.e. at levels of ventilatory assist exceeding both zero assist and PEEP assist levels, and can be performed dynamically during ongoing ventilatory treatment of the patient. This is in contrast to methods according to prior art, requiring occlusion manoeuvres or at least intermittent periods of zero assist ventilation or PEEP assist ventilation. Consequently, the proposed method allows NME to be dynamically and accurately determined while causing less discomfort to the ventilated patient. The relative small interventions required for NME determination using the proposed principles allows the method to be carried out more frequently than corresponding methods according to prior art. Moreover, patient safety is increased since NME can be determined at higher levels of ventilatory assist than before, thereby allowing NME to be determined during adequate ventilatory treatment of the patient.

The samples are typically obtained during at least one breath delivered to the patient at the first level of ventilatory assist and at least one breath delivered to the patient at the second level of ventilatory assist. The samples may be obtained during inspiration and/or expiration. Preferably, the samples are obtained at least during inspiration, in which case the patient flow is an inspiratory flow of breathing gas and the change in lung volume is an increase in lung volume caused by the inspiratory flow. In case obtained during expiration, the patient flow is an expiratory flow of expiration gases and the change in lung volume is a decrease in lung volume caused by the expiratory flow. Samples may be obtained during both inspiration and expiration.

The determination of NME may comprise solving, with respect to NME, an equation describing a relationship between NME, airway pressure, patient flow, lung volume variation (i.e., the change in lung volume caused by the patient flow), electrical activity of a respiratory muscle, and resistance and elastance of the respiratory system of the patient.

For example, NME may be determined by inserting a plurality of sets of the samples into the equation so as to form an overdetermined system of equations, and solving the overdetermined system of equations with respect to NME and any or both of the airway resistance and the elastance of the respiratory system of the patient. Preferably, the overdetermined system of equations is solved with respect to all the parameters NME, R and E, thereby providing for simultaneous determination of the resistive and elastic status of the respiratory system of the patient and the neuromechanical efficiency of the patient.

The equation is preferably based on the relationship:

$$P_{aw} = P_0 + R \cdot \emptyset + E \cdot V - \text{NME} \cdot E_m$$

where $P_{aw}$ is the airway pressure, $P_0$ is the lung pressure at start of inspiration or end of expiration (i.e., when V=0), R and E is the resistance and elastance, respectively, of the respiratory system of the patient, $\emptyset$ is the patient flow, i.e. the volumetric flow rate into or out of the lungs, V is the change in lung volume caused by the patient flow, NME is the neuromechanical efficiency of the respiratory muscle, and $E_m$ is the electrical activity of the respiratory muscle.

Preferably, both the first and second levels of ventilatory assist are well above zero assist, and also well above any PEEP assist level, such that ventilation at both levels of ventilatory assist offers substantial unloading of the lungs of the patient. At the same time, there should be a substantial difference between the first and second levels of ventilatory assist in order to cause a change in one or more of the sampled quantities (airway pressure, inspiratory flow, inspiratory volume and electrical activity of respiratory muscle) that is big enough to enable reliable determination of NME. To this end, the first and second levels of ventilatory assist should preferably differ from each other by at least 10%, more preferably at least 20%, and most preferably at least 30%. The ventilatory assist provided by the breathing apparatus may, for example, be defined as an inspiratory pressure applied to the airways of the patient to facilitate inspiration, or by an inspiratory volume (tidal volume) delivered to the patient during inspiration, depending on the mode of support ventilation currently being provided to the patient. Consequently, the difference in ventilatory assist between the first and the at least second level of ventilatory assist may be a difference in inspiratory pressure or tidal volume delivered by the breathing apparatus.

The respiratory muscle may, for example, be the diaphragm of the patient. This is advantageous in that a signal (Edi signal) representing the electrical activity of the diaphragm (Eadi) may be reliably captured by an Edi catheter, sometimes referred to as a NAVA catheter, inserted into the oesophagus of the patient. The method may advantageously be performed during ventilation of the patient in NAVA mode, in which ventilatory assist is provided to the patient by the breathing apparatus in proportion to the electrical activity of the diaphragm.

When the patient is ventilated in NAVA mode, the method typically comprise a step of automatically switching between the first and second levels of ventilatory assist by changing a ventilator parameter determining the proportion of ventilatory assist in relation to the electrical activity of the diaphragm, for example the ventilator parameter normally referred to as NAVA level or NAVA gain (NAVAg) in the field of NAVA.

The method may further comprise a step of automatically controlling the level of ventilatory assist provided to the patient by the breathing apparatus based on the determined NME. For example, when the breathing apparatus is operated in NAVA mode, this may be achieved by setting the NAVA level based on the determined NME. When operated in another support mode, such as mode of pressure support ventilation (PSV) or volume support ventilation (VSV), the level of ventilatory assist provided to the patient by the breathing apparatus may be controlled based on the determined NME by determining an inspiratory pressure or volume (tidal volume) delivered to the patient based on the determined NME.

Also, the method may comprise a step of generating an alarm signal based on the determined NME.

In some embodiments, the method may comprise the steps of comparing the determined NME value with one or more previously determined NME values, determining a trend for the NME of the patient based on the comparison, and controlling the level of ventilatory assist provided to the patient by the breathing apparatus, and/or generating an alarm signal, based on the determined NME trend.

The proposed method may be performed intermittently during ongoing ventilation of the patient. Between determinations of the physiological parameters, including NME, the patient may be ventilated at a baseline level of ventilatory assist. When determination is to be made, samples of airway pressure, patient flow lung volume variation and electrical activity of the respiratory muscle may be obtained during at least one respiratory cycle (i.e., breath) at the baseline level of ventilatory assist. After the at least one respiratory cycle at the baseline level of ventilatory assist, the level of ventilatory assist is changed to a temporary level of ventilatory assist for at least one respiratory cycle. During the at least one respiratory cycle at the temporary level of ventilatory assist, more samples of airway pressure, patient flow, lung volume variation and electrical activity of the respiratory muscle are obtained. After the at least one respiratory cycle at the temporary level of ventilatory assist, ventilation returns to the baseline level of ventilatory assist, at which it may be maintained until next intermittent determination of the physiological parameters. The temporary level of ventilatory assist may be either higher or lower than the baseline level of ventilatory assist.

During ongoing ventilation, the baseline level of ventilatory assist may be continuously or intermittently adjusted to the current need of unloading of the patient's lungs. This may be achieved by controlling the level of ventilatory assist provided to the patient based on the determined NME. For example, the baseline level of ventilatory assist can be adapted to the current needs of the patient by adapting the baseline level of ventilatory assist to the current neuromuscular efficiency of the patient, as reflected by the most recently determined NME value, or to a more long-term tendency of the neuromuscular efficiency, as reflected e.g. by the above mentioned trend.

The method is typically a computer implemented method that is performed upon execution of a computer program by a control computer of the breathing apparatus. The computer program may be stored in a non-volatile memory of the breathing apparatus.

Consequently, according to another aspect of the present disclosure, there is provided a computer program for determination of at least one physiological parameter, including NME, of a patient connected to a breathing apparatus providing ventilatory assist to the patient, the computer program comprising computer-readable code segments which, when executed by a control computer of the breathing apparatus, causes the breathing apparatus to:

obtain samples of an airway pressure, a patient flow, a change in lung volume caused by the patient flow, and an electrical activity of a respiratory muscle of the patient during ventilation of the patient at a first level of ventilatory assist and at least a second and different level of ventilatory assist, and determine the at least one physiological parameter, including NME, from the airway pressure samples, the patient flow samples, the samples of the change in lung volume, and the samples of the electrical activity of the respiratory muscle, obtained at the different levels of ventilatory assist.

According to yet another aspect of the present disclosure there is provided a breathing apparatus for determination of at least one physiological parameter, including NME, of a patient during provision of ventilatory assist to the patient by the breathing apparatus, the breathing apparatus comprising a set of sensors including at least one pressure sensor, at least one flow sensor, and a bioelectric sensor arrangement for measuring electrical activity of a respiratory muscle of the patient. The breathing apparatus further comprises a control computer for controlling a level of ventilatory assist provided to the patient by the breathing apparatus, the control computer being configured to:

cause the breathing apparatus to ventilate the patient at a first level of ventilatory assist and at least a second and different level of ventilatory assist;

obtain samples of an airway pressure, a patient flow, a change in lung volume caused by the patient flow, and an electrical activity of the respiratory muscle of the patient during ventilation of the patient at each of the different levels of ventilatory assist, and determine the at least one physiological parameter, including NME, from the airway pressure samples, the patient flow samples, the samples of the change in lung volume, and the samples of electrical activity of the respiratory muscle, obtained at the different levels of ventilatory assist.

The control computer may be configured to determine the at least one physiological parameter by solving with respect to NME an equation describing a relationship between NME, airway pressure, patient flow, lung volume variation, electrical activity of a respiratory muscle, airway resistance and elastance of the lungs of the patient, for example the above mentioned equation $$P_{aw} = P_0 + R \cdot \emptyset + E \cdot V - \text{NME} \cdot E_m$$

The control computer may be configured to insert a plurality of sets of the samples into the equation so as to form an overdetermined system of equations, and to solve the overdetermined system of equations with respect to NME and any or both of the airway resistance (R) and the elastance (E) of the respiratory system of the patient. Preferably, the control computer is configured to solve the overdetermined system of equations with respect to all of the parameters NME, R and E, thereby providing for simultaneous determination of the resistive and elastic status of the respiratory system of the patient and the neuromechanical efficiency of the patient.

The breathing apparatus is preferably configured to use the electrical activity of the respiratory muscle not only in the determination of the at least one physiological parameter but also in the control of the mechanical ventilation provided to the patient. The breathing apparatus may, for example, be configured to be operated in a neurally controlled mode in which the measured electrical activity of the respiratory muscle is used by the control computer to determine the timing and/or size of breaths delivered to the patient. According to one example, the measured electrical activity of the respiratory muscle may be used to trigger delivery of breaths to the patient, for example in a pressure support mode in which the pressure delivered to the patient during inspiration is proportional to the measured electrical activity of the respiratory muscle. The measured electrical activity may also be used by the breathing apparatus to provide for continuous neutrally controlled pressure support to the patient during the entire respiratory cycle, i.e., during both inspiration and expiration. In this case, the pressure applied to the patient may be controlled based on the electrical activity of the respiratory muscle during both inspiration and expiration, for example by applying a pressure that is proportional to the electrical activity of the respiratory muscle to the airways of the patient during both inspiration and expiration.

The breathing apparatus is preferably a NAVA-enabled breathing apparatus, such as a ventilator adapted for operation in a NAVA mode, configured to provide ventilatory assist to the patient in synchrony with and proportion to the electrical activity of a respiratory muscle, such as the diaphragm, of the patient. In some embodiments, the control computer may be configured to receive an Edi signal representing the electrical activity of the patient's diaphragm from a bioelectric sensor comprising an Edi catheter, inserted into the oesophagus of the patient, and to control the breathing apparatus to provide ventilatory assist to the patient in synchrony with and proportion to the received Edi signal. The control computer of the breathing apparatus may, thus, be configured to use a bioelectric signal representing the electrical activity of a respiratory muscle of the patient both to control the ventilatory assist provided to the patient by the breathing apparatus, and in the determination of NME.

The switching between the first and second levels of ventilatory assist may be performed automatically by the control computer of the breathing apparatus. For example, the control computer may be configured to switch from the first to the second level of ventilatory assist, or vice versa, by changing the set NAVA level, as discussed above. As also discussed above, the difference between the first and second levels of ventilatory assist, for example in terms of an inspiratory pressure applied to the patient at the respective level of ventilatory assist or a tidal level delivered to the patient at the respective level of ventilatory assist, should be at least 10%, preferably at least 20%, and most preferably at least 30%.

In some embodiments, the control computer may be configured to control a level of ventilatory assist provided to the patient by the breathing apparatus based on the determined NME. For example, as discussed above, the control computer may be configured to automatically adjust a baseline level of ventilatory assist to be provided to the patient based on the determined NME.

More advantageous aspects of the method, computer program and breathing apparatus of the present disclosure will be described in the detailed description following hereinafter.

BRIEF DESCRIPTION OF DRAWINGS

A more complete appreciation of the invention disclosed herein will be obtained as the same becomes better understood by reference to the following detailed description when considered in conjunction with the accompanying drawings briefly described below, in which drawings the same reference numerals are used to represent corresponding functional elements.

DETAILED DESCRIPTION

A breathing apparatus and an associated method for automatic and dynamic determination of at least one physiological parameter, including the neuromechanical efficiency (NME), of a patient being ventilated by the breathing apparatus will now be described with reference to an exemplary and non-limiting embodiment.

Figure 1:
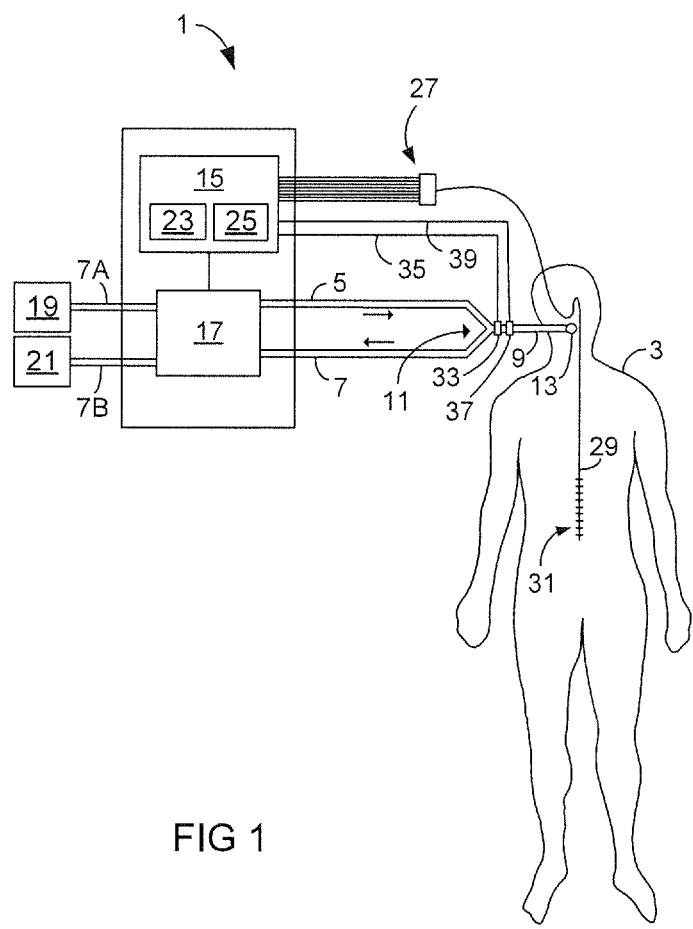
FIG. 1 illustrates schematically an exemplary embodiment of a breathing apparatus for determination of at least one physiological parameter, including NME, during provision of ventilatory assist to the patient by the breathing apparatus.

FIG. 1 illustrates a breathing apparatus 1, such as a ventilator or an anaesthesia machine, for mechanical ventilation of a patient 3. The breathing apparatus 1 is connected to the patient 3 via an inspiratory line 5 for supplying breathing gas to the patient 3, and an expiratory line 7 for conveying expiration gas away from the patient 3. The inspiratory line 5 and the expiratory line 7 are connected to a common line 9, via a so called Y-piece 11, which common line is connected to the patient 3 via a patient connector 13, such as a facemask or an endotracheal tube.

The breathing apparatus 1 further comprises a control unit or control computer 15 for controlling the ventilation of the patient 3 based on pre-set parameters and/or measurements obtained by various sensors of the breathing apparatus. The control computer 15 controls the ventilation of the patient 3 by controlling a pneumatic unit 17 of the breathing apparatus 1, which pneumatic unit 17 is connected on one hand to one or more gas sources 19, 21 and on the other hand to the inspiratory line 5 for regulating a flow and/or pressure of breathing gas delivered to the patient 3. To this end, the pneumatic unit 17 may comprise various gas mixing and regulating means well known in the art of ventilation, such as gas mixing chambers, controllable gas mixing valves, turbines, controllable inspiration and/or expiration valves, etc.

The control computer 15 comprises a processing unit 23, such as a microprocessor, and a non-volatile memory hardware device 25 storing a computer program for controlling the operation of the breathing apparatus 1 and determining the NME of the patient 3 in accordance with the principles described herein. Unless stated otherwise, actions and method steps described hereinafter are performed by, or caused by, the control computer 15 of the breathing apparatus 1 upon execution by the processing unit 23 of different code segments of the computer program stored in the memory 25.

The breathing apparatus 1 further comprises a bioelectric sensor arrangement 27 coupled to the control computer 15 of the breathing apparatus 1. The bioelectric sensor arrangement 27 is configured to detect bioelectric signals indicative of the patient's efforts to breathe and to provide the bioelectric signals to the control computer 15 for use in the determination of the NME of the patient 3, as will be described below.

In the exemplary embodiment illustrated in FIG. 1, the bioelectric sensor arrangement 27 is an EMG detector for recording the diaphragm EMG of the patient 3. To this end, the sensor arrangement 27 comprises an oesophageal catheter 29 carrying an array of electrodes 31 for capturing myoelectrical signals (EMG signals) from the diaphragm of the patient 3. The electrodes 31 produce a number of subsignals that are processed by the control computer 15 to calculate a signal, the Edi signal, representing the electrical activity of the diaphragm (Eadi) and so indicative of the patient's efforts to breathe. Since the EMG signals captured by the sensor are used to calculate an Edi signal, the oesophageal catheter 29 is often referred to as an Edi catheter within the field of ventilation.

Although exemplified in form of an Edi catheter, it should be understood that the bioelectric sensor arrangement 27 could be any known bioelectric sensor arrangement for detection of bioelectric signals originating from a respiratory muscle of a patient and indicative of the patient's effort to breath. For example, the bioelectric sensor arrangement 27 could comprise a number of surface electrodes placed on the ribcage, the abdomen or in the vicinity of the phrenic nerve of the patient 3 to sense and filter out diaphragmatic EMG signals to be used in the calculation of NME. According to another example, the bioelectric sensor arrangement could be devised to detect laryngopharyngeal EMG signals of the patient 3, indicative of the electric activity of respiratory muscles in the laryngopharyngeal region of the patient 3, e.g. the thyroarytenoid and cricothyroid muscles, and to use the laryngopharyngeal EMG signals in the determination of the NME. Examples of suitable bioelectric sensor arrangements for detection of laryngopharyngeal EMG signals that may be used in the determination of NME are disclosed in international patent application WO2016/153406 by the same applicant.

The breathing apparatus 1 may be any type of breathing apparatus operated in any type of support ventilation mode, such as a mode of pressure support ventilation (PSV) or volume support ventilation (VSV). In such a scenario, in which the patient 3 is ventilated in a ventilation mode that is completely independent of the bioelectric signal captured by the bioelectric sensor arrangement 27, the bioelectric signal may be captured and used for the sole purpose of determining the NME of the patient using the principles described herein.

Preferably, however, the breathing apparatus 1 is configured to be operated in a bioelectrically controlled mode of ventilation in which the control computer 15 controls the pneumatic unit 17 and hence the ventilation of the patient 3 based on the bioelectric signals detected by the bioelectric sensor arrangement 27.

That the control computer 15 controls the ventilation of the patient 3 based on the bioelectric signal captured by the bioelectric sensor arrangement 27 means that the bioelectric signal is used by the control computer 15 at least for the triggering of breaths that are to be delivered to the patient 3, i.e., for determining the onset time of inspiration phases. The bioelectric signal may also be used by the control computer 15 to control other breath-related parameters, such as the airway pressure applied during the breath, the time for cycle off of the breath, etc. Preferably, the bioelectric signal is used by the control computer 15 to control both the timing and the magnitude of the breaths delivered to the patient 3.

In the illustrated embodiment, the breathing apparatus 1 is configured to be operated in NAVA mode in which the Edi signal captured by the bioelectric sensor arrangement 27 is used to deliver breathing gas to the patient 3 in synchrony with and in proportion to the patient's own efforts to breathe, as described in greater detail in, for example, WO1998/48877, WO1999/62580, WO2006/131149, and WO2008/131798.

Besides the bioelectric signal representing the electrical activity of a respiratory muscle of the patient 3, the control computer 15 of the breathing apparatus 1 is further configured to obtain measurements of a patient flow, for example an inspiratory flow of breathing gas delivered to the patient 3 during inspiration. To this end, the breathing apparatus 1 may comprise a flow sensor 33 for measuring the inspiratory flow delivered the patient 3 during inspiration phases. Preferably, the flow sensor 33 is configured to measure also an expiratory flow of expiration gas exhaled by the patient during expiration phases. In the exemplary embodiment illustrated in FIG. 1, the flow sensor 33 is located in or close to the Y-piece 11 and configured to measure both inspiratory and expiratory flows. The measurement signals obtained by the flow sensor 33 are transmitted to the control computer 15 via a signalling line 35, whereby the measurement signals are used by the control computer 15 in the determination of the NME of the patient 3, as will be described below. In other embodiments, a first flow sensor for measuring the inspiratory flow of breathing gas delivered to the patient 3 may be arranged within an inspiratory module of the breathing apparatus 1, whereas a second flow sensor for measuring an expiratory flow of expiration gas exhaled by the patient may be arranged within an expiratory module of the breathing apparatus 1. The patient flow measurements are further used by the control computer 15 to calculate changes in the patient's lung volume, i.e. a lung volume variation, caused by the patient flow, which changes in lung volume are subsequently used in the calculation of NME.

Furthermore, the control computer 15 is configured to obtain measurements of a pressure applied to the patient 3 during inspiration and/or expiration, for example from a pressure sensor 37 of the breathing apparatus 1. In the exemplary embodiment illustrated in FIG. 1, the pressure sensor 37 is located in or close to the Y-piece 11 and configured to measure a pressure substantially corresponding to the airway pressure of the patient 3. The measurement signals obtained by the pressure sensor 37 are transmitted to the control computer 15 via a signalling line 39, whereby the measurement signals are used by the control computer 15 in the determination of the NME of the patient 3, as will be described below. In other embodiments, one or more pressure sensors for measuring one or more pressures from which the airway pressure of the patient 3 can be derived may be arranged within an inspiratory module and/or an expiratory module of the breathing apparatus 1.

The breathing apparatus 1 and, more specifically, the control computer 15 of the breathing apparatus 1, is configured to calculate physiological, patient-related parameters, including NME, based on samples obtained by the bioelectric sensor arrangement 27, the flow sensor 33, and the pressure sensor 37. The rationale behind the NME calculation will now be described with reference to FIG. 2.

Figure 2:
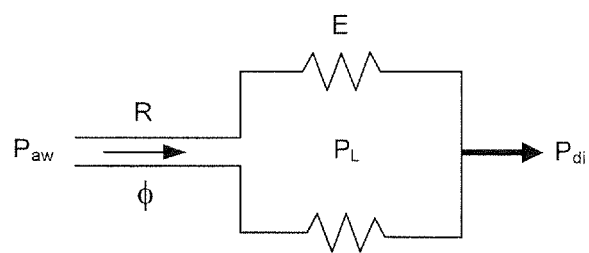
FIG. 2 illustrates a simplified, single-compartment lung model which may be used as starting point for NME determination according to some aspects of the present disclosure.

FIG. 2 illustrates a simplified, single-compartment lung model, according to which the following mathematical relationships prevail, given that there is no contribution of muscular force from the diaphragm:

$$P_{aw} = P_L + R \cdot \varnothing \quad \text{(Eq. 1)}$$

$$P_L = P_0 + E \cdot V \quad \text{(Eq. 2)}$$

where $P_{aw}$ is the airway pressure, $P_L$ is the lung pressure, R is the resistance to flow of gas into or out of the lung, i.e. the resistance of the respiratory system, $\varnothing$ is the patient flow, i.e. the volumetric flow rate of gas flowing into or out of the lung, V is the change in lung volume caused by the patient flow, $P_0$ is the pressure in the lung at the start of inspiration or at the end of expiration (i.e., when V=0), and E is the elastance of the lung (which is equal to the inverse of the lung compliance, 1/C). It should be noted that in the equations, patient flow Ø is treated as positive in the direction of inspiratory flow and negative in the direction of expiratory flow.

Combining equations 1 and 2 yields the following expression, sometimes referred to as the equation of motion of the respiratory system:

$$P_{aw}=P_0+R\cdot\emptyset+E\cdot V \qquad (Eq.\ 3)$$

The change in lung volume is not only caused by changes in the lung pressure $P_L$. The muscular force of the diaphragm, caused by a transdiaphragmatic pressure, $P_{di}$, generated by the diaphragm, also affects the change in lung volume. Taking the transdiaphragmatic pressure into account, equation 2 can be modified in accordance with:

$$P_L+P_{di}=P_0+E\cdot V \qquad (Eq.\ 4)$$

The transdiaphragmatic pressure, $P_{di}$, can be assumed to be directly proportional to the captured Edi signal, using a constant of proportionality that is indicative of the neuromuscular efficiency of the diaphragm, i.e. the NME. Consequently, assuming that $P_{di}=NME\cdot Edi$, equation 4 can be modified in accordance with:

$$P_L=P_0+E\cdot V-NME\cdot Edi \qquad (Eq.\ 5)$$

By combining equations 1 and 5, the airway pressure, $P_{aw}$, may be expressed in accordance with the following equation:

$$P_{aw}=P_0+R\cdot\emptyset+E\cdot V-NME\cdot Edi \qquad (Eq.\ 6)$$

By obtaining samples of the readily measurable or derivable parameters airway pressure ($P_{aw}$), patient flow (Ø), lung volume variation (V) and Edi during one or more respiratory cycles (breaths), and inserting each set of samples into equation 6, an overdetermined system of equations allowing determination of the unknown parameter quadruple $\{P_0, R, E, NME\}$ can be formed in accordance with:

$$\underbrace{\begin{pmatrix} \vdots \\ P_{aw} \\ \vdots \end{pmatrix}}_{b} = \underbrace{\begin{pmatrix} \vdots & \vdots & \vdots & \vdots \\ 1 & \emptyset & V & -Edi \\ \vdots & \vdots & \vdots & \vdots \end{pmatrix}}_{A} \cdot \underbrace{\begin{pmatrix} P_0 \\ R \\ E \\ NME \end{pmatrix}}_{x} \qquad (Eq.\ 7)$$

The overdetermined system of equations 7 may, for example, be solved by finding the least square solution in accordance with:

$$x=(A^T\cdot A)^{-1}\cdot(A^T\cdot b) \qquad (Eq.\ 8)$$

where $(A^T\cdot A)$ and its inverse $(A^T\cdot A)^{-1}$ are 4×4 square matrices and $(A^T\cdot b)$ is a 4×1 column vector.

The $P_{aw}$, Ø, V and Edi samples may be obtained through direct measurements and/or as estimates calculated from other measurable quantities. The Edi samples may, for example, be obtained by sampling the captured Edi signal. The samples of $P_{aw}$ and Ø may, for example, be obtained from direct measurements of $P_{aw}$ and Ø, obtained by the pressure sensor 37 and the flow sensor 33, respectively, or by calculating $P_{aw}$ and Ø from pressure and flow measurements obtained elsewhere in the breathing circuit. The samples of V may, for example, be obtained by integrating the measured flow with respect to time.

The system of equations, Eq. 7, can be unambiguously solved with a high degree of certainty as long as at least some of the sampled parameters vary during the sample period. Therefore, in order to obtain reliable measures of the unknown physiological parameters $P_0$, R, E and NME, the samples are preferably obtained during ventilation of the patient 3 at two different levels of ventilatory assist. For example, the control computer 15 may be configured to cause the breathing apparatus 1 to provide at least a first breath to the patient 3 at a first level of ventilatory assist and at least a second breath at a second and different level of ventilatory assist, and to determine the unknown physiological parameters from samples obtained during breaths provided at the different levels of ventilatory assist. The determination may be made intermittently at regular or irregular time intervals, or upon request from an operator of the breathing apparatus 1.

For example, the breathing apparatus 1 may ventilate the patient 1 at a desired baseline level of ventilatory assist that is adapted to the needs of the patient. When determination of NME is to be made, the control computer 15 may cause the breathing apparatus 1 to temporarily deliver at least one breath at a different level of ventilatory assist, whereby the determination can be made based on samples obtained at the different levels of ventilatory assist. After one or a few breaths at the temporary level of ventilatory assist, the control computer 15 may cause the breathing apparatus to switch back to "normal operation", whereby breaths are once again delivered to the patient at the baseline level of ventilatory assist.

Since the only requirement of the different levels of ventilatory assist is that the change in ventilatory assist from one level to another induces a sufficient change in one or more of the sampled parameters, both levels of ventilatory assist can be high enough to ensure adequate ventilation of the patient. Preferably, both levels are well above a zero assist level at which the patient does not receive any ventilatory assist at all, and also above any PEEP assist level potentially set for the ventilatory treatment. A PEEP assist level may in this regard be seen as a minimum level of ventilatory assist required to keep the airways of the patient 3 open at the end of expiration, i.e., to prevent or mitigate end-expiratory alveolar collapse.

Typically, a difference in ventilatory assist of 10% between the first and second levels of ventilatory assist is sufficient to provide for reliable determination of the unknown parameters. Preferably, however, the difference should be at least 20%, and even more preferably at least 30%. The ventilatory assist provided by a breathing apparatus, such as a ventilator, may, as well known in the art, be expressed in terms of the inspiratory pressure applied to the airways of the patient or the inspiratory volume (tidal volume) of breathing gas delivered to the patient during a breath. Consequently, the difference between the first and second levels of ventilatory assist should be at least 10%, preferably at least 20%, and even more at least 30%, in terms of inspiratory pressure or volume.

Clearly, not only does the proposed methodology allow for dynamic and non-invasive determination of NME without subjecting the patient to drastic interventions, such as zero-assist or occlusion manoeuvres, the determination of the unknown parameter quadruple $\{P_0, R, E, NME\}$ also provides clinically important information relating to the resistive and elastic properties of the patient's respiratory system.

The change in ventilatory assist from the first level to the second level, or vice versa, may be effectuated in different ways depending on the mode of support ventilation currently being provided to the patient. For example, if operated in a pressure support mode or a volume support mode, the level of ventilatory assist provided to the patient may be changed by adjusting the inspiratory pressure applied to the patient or the volume (tidal volume) delivered to the patient during inspiration.

When operated in NAVA mode, the level of ventilatory assist is preferably changed by changing the NAVA level setting often referred to as NAVAg (NAVA gain), which setting determines the inspiratory pressure applied to the patient in relation to the electrical activity of the diaphragm. As well known in the art, the set NAVA level reflects the amount of work of breathing that the breathing apparatus will take over from the patient. Typically, the breathing apparatus is configured to deliver breathing gas to the patient at an inspiratory pressure that is proportional to the measured Edi signal, whereby the constant of proportionality between the measured Edi signal and the applied inspiratory pressure is adjusted by changing the NAVA level.

The change in ventilatory assist may be performed automatically by the breathing apparatus 1 and the magnitude of the change, i.e. the difference in ventilatory assist between the first and the at least second level of ventilator assist, may be predefined or dynamically determined by the control computer 15 based on sensor measurements. For example, the control computer 15 may be configured to calculate an error or uncertainty in the determination of NME from the correlation of the sampled quantities, and to increase the difference in ventilatory assist between the first and the at least second level of ventilatory assist if the error or uncertainty exceeds a certain threshold value.

In alternative embodiments, more sophisticated mathematical models may be employed in the determination of the unknown physiological parameters. For example, the resistance of the patient's respiratory system, R, may be assumed to vary as a function of flow, Ø, and the elastance of the lungs of the patient, E, may be assumed to vary as a function of lung volume, V, in accordance with:

$$R = R_1 + R_2 \cdot |Ø| \quad \text{(Eq. 9)}$$

$$E = E_1 + E_2 \cdot V \quad \text{(Eq. 10)}$$

Combining equations 2 and 10 yields:

$$P_L(V) = P_0 + E_1 \cdot V + \tfrac{1}{2} E_2 \cdot V^2 \quad \text{(Eq. 11)}$$

Likewise, the neuromuscular efficiency, NME, of the diaphragm can be assumed to vary as a function of lung volume to account for the decrease in muscular force of the diaphragm with increasing inspiratory lung volume, in accordance with:

$$NME = NME_0 \cdot (1 - \alpha \cdot V) \quad \text{(Eq. 12)}$$

An overdetermined system of equations, corresponding to equation 7 above, could then be formulated as:

$$\underbrace{\begin{pmatrix} \vdots \\ P_{aw} \\ \vdots \end{pmatrix}}_{b} = \underbrace{\begin{pmatrix} \vdots & \vdots & \vdots & \vdots & \vdots & \vdots & \vdots \\ 1 & Ø & |Ø| \cdot Ø & V & \tfrac{1}{2}V^2 & -Edi & V \cdot Edi \\ \vdots & \vdots & \vdots & \vdots & \vdots & \vdots & \vdots \end{pmatrix}}_{A} \cdot \underbrace{\begin{pmatrix} P_0 \\ R_1 \\ R_2 \\ E_1 \\ E_2 \\ NME_0 \\ NME_0 \cdot \alpha \end{pmatrix}}_{x} \quad \text{(Eq. 13)}$$

This overdetermined system of equations can then be solved with respect to the parameters found in the 1×7 vector column on the right hand side, e.g. using the method of least squares, whereby the physiological parameters R, E and NME can be determined from equations 9, 10 and 12.

In yet alternative embodiments, the inertia of the respiratory system may be accounted for by modifying equation 2 to read:

$$P_{aw} = P_L + R \cdot Ø + I \cdot \dot{\phi} \quad \text{(Eq. 14)}$$

where $\dot{\phi}$ is the derivative of the volumetric flow, Ø, with respect to time.

As understood by the skilled person, an overdetermined system of equations corresponding to equations 7 and 13 could then be set up and solved using the above described principles, whereby the unknown physiological parameters R, E and NME could be determined taking the inertia of the respiratory system into account.

Although described in the context of an exemplary embodiment in which an Edi catheter inserted into the oesophagus of the patient 3 is used to capture the Edi signal, it should be understood that the electrical activity of the patient's diaphragm may be captured also using other types of sensors. For example, the diaphragmatic EMG may be captured by a set of surface electrodes placed on the ribcage, the abdomen or in the vicinity of the phrenic nerve of the patient 3, and used to calculate the Edi signal or a corresponding signal that may be used in the calculations of the unknown parameters in accordance with the above described principles.

In the above examples, an Edi signal indicative of the electrical activity of the diaphragm of the patient 3 has been captured and used in the determination of the unknown physiological parameters, including NME. However, it should be understood that the same or similar principles may be applied to assess the neuromuscular efficiency of the diaphragm and the resistive and elastic properties of the respiratory system of the ventilated patient 3 by capturing and using bioelectric signals indicative of the electrical activity of respiratory muscles other than the diaphragm. For example, laryngopharyngeal EMG signals indicative of the electrical activity of respiratory-related muscles in the laryngopharyngeal region, such as the thyroarytenoid and cricothyroid muscles, captured and processed in accordance with the principles described in WO2016/153406, may be used in a similar manner to calculate the parameters R, E and NME. In such a scenario, the laryngopharyngeal EMG signals can be assumed to be proportional to the electrical activity of the diaphragm and hence the Edi signal, which makes it possible to conduct the above calculations by replacing Edi with a parameter that is indicative of the measured laryngopharyngeal EMG. In general, any bioelectric signal indicative of electrical activity of a muscle participating in the work of breathing of the ventilated patient may be used. As long as the electrical activity of the muscle measured upon depends on the strength of the breathing signals sent from the respiratory centre of the patient's brain, the calculated NME value will indicate the capability of the diaphragm to generate muscle force in response to breathing signals sent from the brain's respiratory centre and, thus, the neuromuscular efficiency of the diaphragm.

Therefore, equation 6 may be generalized to:

$$P_{aw} = P_0 + R \cdot Ø + E \cdot V - NME \cdot E_m \quad \text{(Eq. 15)}$$

where $E_m$ is a parameter indicative of the electrical activity of any breathing muscle generating measurable electrical activity in response to breathing signals sent from the respiratory centre of the brain. The unknown physiological parameters R, E and NME can then be determined from samples of $P_{aw}$, Ø, V and $E_m$ by finding a solution to an overdetermined system of equations, as described above.

As mentioned above, the elastance, E, is the inverse of the lung compliance, C. Consequently, as understood by the skilled person, the above equations could be modified by exchanging E for 1/C without diverting from the principles of the present disclosure. For example, exchanging E for 1/C in equation 15 would result in the following equation:

$$V = C \cdot P_{aw} - C \cdot P_0 - C \cdot R \cdot \text{Ø} + C \cdot \text{NME} \cdot E_m \quad \text{(Eq. 16)}$$

Inserting the sets of samples into equation 16 would result in an overdetermined system of equations from which the parameters {C, C·$P_0$, C·R, C·NME} could be determined, e.g. through the method of least squares. Once the lung compliance, C, has been determined, the unknown parameters $P_0$, R and NME can all be calculated.

Figure 3:
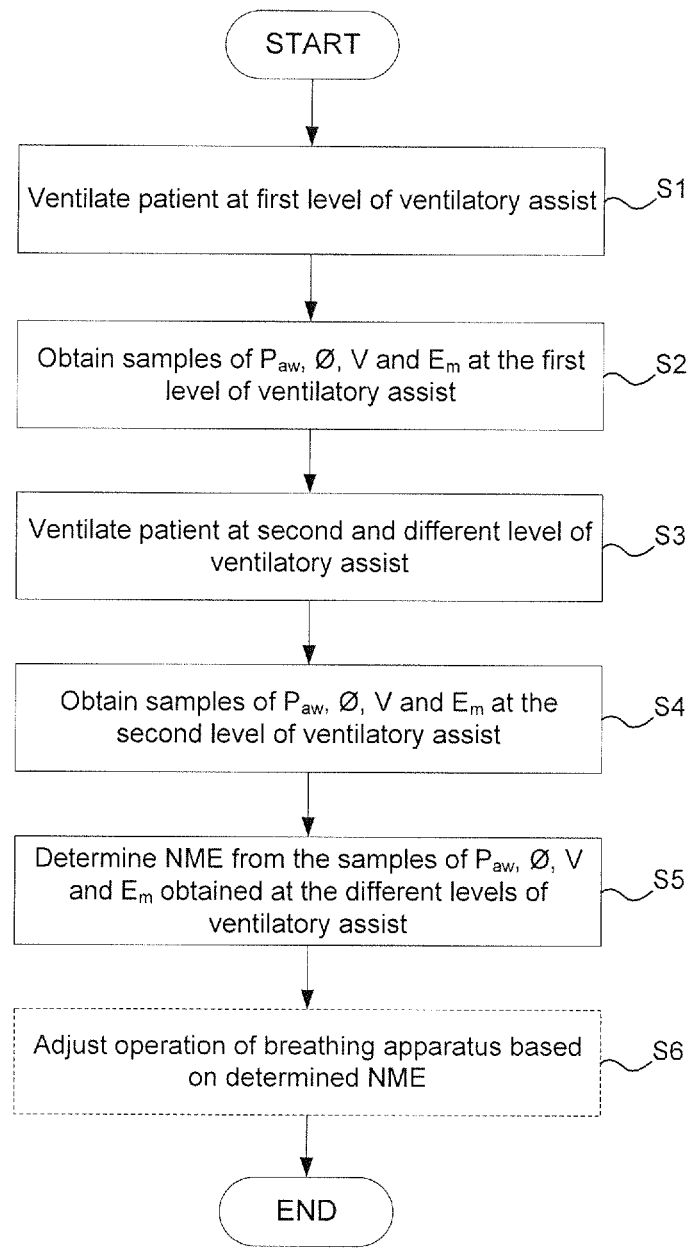
FIG. 3 is a flow chart illustrating an exemplary embodiment of a method for determination of at least one physiological parameter, including NME, of a mechanically ventilated patient.

FIG. 3 is a flow chart illustrating a method for determination of at least one physiological parameter, including NME, of a mechanically ventilated patient. The method is preferably a computer implemented method that is automatically performed by the breathing apparatus 1 upon execution by the control computer 15 of a computer program stored in the non-volatile memory 25, which computer program comprises instructions that cause the breathing apparatus to perform the various method steps.

In a first step, S1, the patient is ventilated at a first level of ventilatory assist, meaning that at least one breath is delivered to the patient at the first level of ventilatory assist. Preferably, the first level of ventilatory assist is a baseline level of ventilatory assist that is adapted to the needs of the patient.

In a second step, S2, samples of an airway pressure, $P_{aw}$, a patient flow, Ø, change in lung volume V caused by the patient flow, and an electrical activity of a respiratory muscle of the patient, $E_m$, are obtained at the first level of ventilatory assist. As mentioned above, the samples of the electrical activity of a respiratory muscle may, for example, be samples of an Edi signal indicative of the electrical activity of the patient's diaphragm.

In a third step, S3, the level of ventilatory assist is changed to a second level of ventilatory assist that is different than the first level of ventilatory assist. At least one breath is delivered to the patient at the second level of ventilatory assist. Both the first and the second levels of ventilatory assist are above a zero level of ventilatory assist and above any level of ventilatory assist provided by the potential application by the breathing apparatus of a PEEP to the patient.

In a fourth step, S4, samples of the airway pressure, $P_{aw}$, the patient flow, Ø, the change in lung volume, V, and the electrical activity of the respiratory muscle are obtained also at the second level of ventilatory assist.

In a fifth step, S5, the at least one physiological parameter, including NME, is determined from the airway pressure samples, the patient flow samples, the samples of the change in lung volume, and the samples of the electrical activity of the respiratory muscle, obtained at the different levels of ventilatory assist.

In a subsequent and optional step, S6, the operation of the breathing apparatus 1 may be adjusted based on the determined NME value. For example, an alarm signal may be generated by the control computer 15 to alert an operator of the breathing apparatus if the NME value is below a certain threshold value or indicates a decrease in NME over time. Instead or in addition to generating an alarm signal, the control computer 15 may be configured to automatically adjust the level of ventilatory support provided to the patient 3, for example the above mentioned baseline level of ventilatory support, based on the determined NME value or a change in NME over time. If, for example, the determined NME value is below a certain threshold value or tends to decrease over time, the control computer 15 may be configured to increase the baseline level of ventilatory support to compensate for poor or decreasing neuromuscular efficiency of the patient's diaphragm.

The invention claimed is:

1. A computer implemented method for determination of at least one physiological parameter of a patient, the at least one parameter including a neuromechanical efficiency (NME) value, the patient being connected to a breathing apparatus which is configured to provide a ventilatory assist to the patient, comprising:
   providing a ventilation to the patient at a first level of ventilatory assist via the breathing apparatus;
   obtaining, at the first level of ventilatory assist, samples of an airway pressure of the patient, a patient flow, a change in lung volume caused by the patient flow, and an electrical activity of a respiratory muscle of the patient during ventilation of the patient;
   providing a second level of ventilatory assist to the patient via the breathing apparatus, the second level of ventilatory assist being different than the first level of ventilatory assist;
   obtaining, at the second level of ventilatory assist, samples of an airway pressure of the patient, a patient flow, a change in lung, volume caused by the patient flow, and an electrical activity of the respiratory muscle of the patient; and
   determining the at least one parameter including the NME value from the airway pressure samples, the patient flow samples, the samples of the change in lung volume and the samples of the electrical activity obtained at the first level of ventilatory assist and the second level of ventilatory assist.

2. The method of claim 1, wherein both the first level and the at least one second level are above a zero level of ventilatory assist and above any level of ventilatory assist provided by a potential application by the breathing apparatus of a positive end-expiratory pressure to the patient.

3. The method of claim 1, wherein the determining step includes solving with respect to the NME value an equation describing a relationship between the NME value, the airway pressure, the patient flow, the change of lung volume, the electrical activity of the respiratory muscle, and resistance and any of elastance and compliance of the respiratory system of the patient.

4. The method of claim 3, wherein the determining step includes inserting a plurality of sets of the samples into the equation so as to form an overdetermined system of equations, and solving the overdetermined system of equations with respect to the NME value and any combination of the resistance, the elastance and the compliance of the respiratory system of the patient.

5. The method of claim 4, wherein the equation is based on the relationship $$P_{aw} = P_0 + R \cdot \text{Ø} + E \cdot V - \text{NME} \cdot E_m$$

where $P_{aw}$ is the airway pressure, $P_0$ is the lung pressure at start of inspiration or end of expiration, R and E is the resistance and elastance, respectively, of the respiratory system, Ø is the patient flow, V is the change in lung volume caused by the patient flow, NME is the neuromechanical efficiency of the respiratory muscle, and $E_m$ is the electrical activity of the respiratory muscle, or the relationship $$V = C \cdot P_{aw} - C \cdot P_0 - C \cdot R \cdot \emptyset + C \cdot \text{NME} \cdot E_m$$

where C is the compliance of the respiratory system.

6. The method of claim 1, wherein the at least one second level is at least 10% above the first level.

7. The method of claim 1, wherein the at least one second level is at least 20% above the first level.

8. The method of claim 1, wherein the at least one second level is at least 30% above the first level.

9. The method of claim 1, wherein the respiratory muscle is a diaphragm of the patient.

10. The method of claim 9, wherein the method is performed during ventilation of the patient in a ventilation mode of neurally adjusted ventilation assist [NAVA], in which ventilatory assist is provided to the patient by the breathing apparatus in synchrony with and in proportion to an electrical activity of the diaphragm.

11. The method of claim 10, further comprising:
automatically switching between the first level and the at least one second level by changing a NAVA gain [NAVAg] determining a proportion of ventilatory assist provided to the patient in relation to the electrical activity of the diaphragm.

12. The method of claim 1, further comprising:
automatically controlling a level of ventilatory assist provided to the patient by the breathing apparatus and/or automatically generating an alarm signal based on the determined NME value.

13. A computer program for determination of at least one physiological parameter of a patient, the at least one parameter including a neuromechanical efficiency (NME) value, the patient being connected to a breathing apparatus which is configured to provide a level of ventilatory assist to the patient, the computer program comprising computer-readable code segments stored in a non-volatile memory which, when executed by a control computer of the breathing apparatus, causes the breathing apparatus to perform steps of:
providing a ventilation to the patient at a first level of ventilatory assist via the breathing apparatus;
obtaining, at the first level of ventilatory assist, samples of an airway pressure of the patient, a patient flow, a change in lung volume caused by the patient flow, and an electrical activity of a respiratory muscle of the patient;
providing a second level of ventilatory assist to the patient via the breathing apparatus, the second level of ventilatory assist being different than the first level of ventilatory assist;
obtaining, at the second level of ventilatory assist, samples of an airway pressure of the patient, a patient flow, a change in lung volume caused by the patient flow, and an electrical activity of the respiratory muscle of the patient; and
determining the at least one parameter including the NME value from the airway pressure samples, the patient flow samples, the samples of the change in lung volume and the samples of the electrical activity obtained at the first level of ventilatory assist and the second level of ventilatory assist.

14. A breathing apparatus for determination of at least one physiological parameter, the at least one parameter including a neuromechanical efficiency (NME) value, the breathing apparatus, which is configured to provide a ventilatory assist to the patient, connectable to a patient and comprising:
at least one pressure sensor;
at least one flow sensor;
a bioelectric sensor arrangement measuring electrical activity of a respiratory muscle of the patient; and
a control computer controlling a level of ventilatory assist provided to the patient,
wherein the control computer is configured to:
cause the breathing apparatus to ventilate the patient at a first level of ventilatory assist;
obtain, at the first level of ventilatory assist, samples of an airway pressure, a patient flow, a change in lung volume caused by the patient flow, and the electrical activity of the respiratory muscle of the patient;
cause the breathing apparatus to ventilate the patient at a second level of ventilatory assist, the second level of ventilatory assist being different than the first level of ventilatory assist;
obtain, at the second level of ventilatory assist, samples of an airway pressure of the patient, a patient flow, a change in lung volume caused by the patient flow, and an electrical activity of the respiratory muscle of the patient; and
determine the at least one parameter including the NME value from the airway pressure samples, the patient flow samples, the samples of the change in lung volume, and the samples of electrical activity of the respiratory muscle, obtained at the first level of ventilatory assist and the second level of ventilatory assist.

15. The breathing apparatus of claim 14, wherein both the first level and the at least second level are above a zero level of ventilatory assist and above any level of ventilatory assist provided by a potential application by the breathing apparatus of a positive end-expiratory pressure to the patient.

16. The breathing apparatus of claim 14, wherein the control computer is configured to determine the at least one parameter by solving with respect to the NME value an equation describing a relationship between the NME value, the airway pressure, the patient flow, the lung volume variation, the electrical activity of the respiratory muscle, and resistance and any of elastance and compliance of the respiratory system of the patient.

17. The breathing apparatus of claim 16, wherein the control computer is configured to insert a plurality of sets of the samples into the equation so as to form an overdetermined system of equations, and to solve the overdetermined system of equations with respect to the NME value and any combination of the resistance, the elastance and the compliance of the respiratory system of the patient.

18. The breathing apparatus of claim 17, wherein the equation is based on the relationship $$P_{aw} = P_0 + R \cdot \emptyset + E \cdot V - \text{NME} \cdot E_m$$

where $P_{aw}$ is the airway pressure, $P_0$ is the lung pressure at start of inspiration or end of expiration, R and E is the resistance and elastance, respectively, of the respiratory system, $\emptyset$ is the patient flow, V is the change in lung volume caused by the patient flow, NME is the neuromechanical efficiency of the respiratory muscle, and $E_m$ is the electrical activity of the respiratory muscle, or the relationship $$V = C \cdot P_{aw} - C \cdot P_0 - C \cdot R \cdot \emptyset + C \cdot \text{NME} \cdot E_m$$

where C is the compliance of the respiratory system.

19. The breathing apparatus of claim 14, wherein the at least one second level is at least 10% above the first level.

20. The breathing apparatus of claim 14, wherein the at least one second level is at least 20% above the first level.

21. The breathing apparatus of claim 14, wherein the at least one second level is at least 30% above the first level.

22. The breathing apparatus claim 14, wherein the bioelectric sensor arrangement is configured to measure electrical activity of a diaphragm of the patient.

23. The breathing apparatus of claim 22, wherein the breathing apparatus is configured to ventilate the patient in a neurally adjusted ventilation assist [NAVA] ventilation mode in which ventilatory assist is provided to the patient by the breathing apparatus in synchrony with and in proportion to the electrical activity of the diaphragm, and to determine the at least one parameter when operated in the NAVA ventilation mode.

24. The breathing apparatus of claim 23, wherein the control computer is configured to cause the breathing apparatus to switch between the first and the at least one second level by changing a NAVA gain [NAVAg] determining the proportion of ventilatory assist provided to the patient by the breathing apparatus in relation to the electrical activity of the diaphragm.

25. The breathing apparatus of claim 14, wherein the control computer is configured to control the level of ventilatory assist provided to the patient by the breathing apparatus, and/or to generate an alarm signal, based on the determined NME value.

* * * * *